United States Patent [19]

Furihata

[11] 4,300,564
[45] Nov. 17, 1981

[54] FORCEPS FOR EXTRACTING STONES IN THE PELVIS OF A KIDNEY

[75] Inventor: Hiroyuki Furihata, Hamura, Japan

[73] Assignee: Olympus Optical Co., Ltd., Tokyo, Japan

[21] Appl. No.: 90,279

[22] Filed: Nov. 1, 1979

[30] Foreign Application Priority Data

Nov. 9, 1978 [JP] Japan .................................. 53-138265

[51] Int. Cl.³ .......................... A61B 17/28; A61B 1/00
[52] U.S. Cl. ........................................ 128/321; 128/4; 128/328
[58] Field of Search ............... 128/328, 321, 322, 325, 128/326, 319, 356, 7, 4, 5, 6, 8, 3; 81/300; 433/159, 29

[56] References Cited

U.S. PATENT DOCUMENTS

| | | | |
|---|---|---|---|
| 2,208,369 | 7/1940 | Held | 128/319 |
| 2,243,057 | 5/1941 | Wolf | 128/328 |
| 2,911,968 | 11/1959 | Schueler et al. | 128/6 |
| 2,994,321 | 8/1961 | Tischler | 128/751 |
| 3,008,467 | 11/1961 | Morris | 128/328 |
| 4,049,002 | 9/1977 | Kletschka et al. | 128/321 X |
| 4,177,814 | 12/1979 | Knepshield et al. | 128/347 X |

FOREIGN PATENT DOCUMENTS

| | | | |
|---|---|---|---|
| 2032501 | 1/1972 | Fed. Rep. of Germany | 128/328 |
| 7632753 | 3/1977 | Fed. Rep. of Germany | 128/751 |
| 1394733 | 3/1965 | France | 128/328 |
| 126844 | 5/1919 | United Kingdom | 128/7 |

OTHER PUBLICATIONS

*Sklar* Surgical Instruments Catalogue, Suction & Pressure Apparatus 18th Edition (1973).

*Primary Examiner*—Robert W. Michell
*Assistant Examiner*—Michael H. Thaler
*Attorney, Agent, or Firm*—Frishauf, Holtz, Goodman and Woodward

[57] ABSTRACT

A forceps for extracting stones in the pelvis of a kidney comprises a pair of shanks pivotally connected to each other and each having a finger ring at one end, a pair of arms extending from the other ends of the respective shanks away from the finger rings and being curved to deviate from the plane in which the finger rings are moved toward each other and away from each other, and a pair of stone-clamping members secured to the free ends of the arms, respectively, one of said stone-clamping members being a tubular member into which a telescope is inserted. The field of view of the telescope can be widened by moving the stone-clamping members away from each other, making it possible to correctly perceive both size and position of a stone in the pelvis of the kidney. While observing the stone through the telescope, the operator can easily and quickly hold the stone between the clamping members.

6 Claims, 13 Drawing Figures

FORCEPS FOR EXTRACTING STONES IN THE PELVIS OF A KIDNEY

BACKGROUND OF THE INVENTION

This invention relates to a forceps for extracting stones in the pelvis of a kidney.

FIG. 1 shows a typical known forceps 1 for extracting stones in the pelvis of a kidney. The forceps 1 comprises a pair of shanks 3 pivotally connected to each other at an intermediate point. Each shank 3 has a stone-clamping portion 2 at one end and a finger ring 4 at the other end. In one of the finger rings 4 a thumb is inserted, and a forefinger into the other finger ring 4. The forward portion of each shank 3, which includes the stone-clamping portion 2, is curved to deviate from a plane in which the finger rings 4 are moved toward or away from each other. The forward portions of the shanks 3 are inserted into the pelvis of a kidney to the depth shown by the line A—A so that a stone, if any in the pelvis, may be clamped between the clamping portions 2 when the finger rings 4 are moved toward each other and the stone thus may be extracted from the pelvis.

Since it is not known where a stone is located in the pelvis, it would be difficult to bring the stone-clamping portions 2 to clamp the stone therebetween when the forceps 1 is inserted for the first time. In most cases the stone-clamping portions 2 must be repeatedly inserted into the pelvis until they are brought to a position to clamp the stone. Usually it takes a long time to extract the stone out of the pelvis, thus inevitably keeping the patient in pain for a long time. Sometimes, the stone fails to be removed.

To ascertain where a stone exists in the pelvis, X-rays are applied on the pelvis of the kidney. When, however, the stone and the kidney wall have nearly equal X-ray permeabilities, making it impossible to find the stone in the pelvis, the stone must be caught by the stone-clamping portions 2 by a trial and error method.

FIG. 2 shows another known forceps for extracting stones in the pelvis of a kidney, which is provided with a telescope. The forceps comprises a tube 5 bent at an intermediate portion, a pair of jaws 6 provided at the distal end of the tube 5, and a pair of shanks 7 provided at the proximal end of the tube 5. The shanks 7 are pivotally connected to each other at their one end and each have a finger ring at the other end. An operation wire 9 extends through a wire guide tube 8 which extends along the tube 5. The wire 9 is connected at one end to said one end of one of the shanks 7 and at the other end to the proximal end of one of the jaws 6. When the finger rings of the shanks 7 are moved toward each other with the fingers, the wire 9 is pulled to close the jaws 6.

Also extending through the tube 5 is a telescope 10. Through the telescope 10 a stone, if any, in the pelvis of a kidney can been seen. While seeing the stone through the telescope 10, the operator manipulates the shanks 7 thereby to clamp the stone between the jaws 6. Thus it is easy for the operator to find and clamp the stone. However, since the wire 9 fails to transmit the delicate movement of the shanks 7 to the jaws 6, the jaws 6 cannot clamp the stone as readily as the operator wishes to. Another problem with the forceps of FIG. 2 is that the size of the stone in the pelvis cannot be known through the telescope. Thus, even if the jaws 6 successfully clamp the stone, the stone cannot be extracted if it is too large.

SUMMARY OF THE INVENTION

An object of this invention is to provide a forceps for extracting stones in the pelvis of a kidney, with which it is possible to know through a telescope how large a stone is, to clamp the stone in the pelvis unfailingly while observing the stone through the telescope and to extract the stone unfailingly from the pelvis.

Another object of the invention is to provide a forceps for extracting stones in the pelvis of a kidney, stone-clamping members of which can be correctly moved even if a telescope is twisted.

Still another object of the invention is to provide a forceps for extracting stones in the pelvis of a kidney, which has a fluid passage through which a fluid is supplied to the distal ends of shanks constituting the forceps or taken out of the pelvis.

A forceps according to this invention comprises a pair of shanks pivotally connected to each other and each having a finger ring at one end, a pair of elongate arms extending from the other ends of the respective shanks and being curved in the same direction from the plane in which the finger rings are moved toward each other and away from each other, and a pair of stone-clamping members secured to the free ends of the arms, respectively, one of said elongate arms being a tubular member into which a front viewing telescope is to be inserted. The field of view of the telescope can be widened by moving the stone-clamping members away from each other, making it possible to correctly perceive both size and position of a stone in the pelvis of the kidney. While viewing the stone through the telescope, the operator can easily and quickly hold the stone between the stone-clamping members.

The other of the arms may be made of a tubular member. In this case it is used as a fluid passage.

Further, the stone-clamping members may be painted different colors. The clamping members in the pelvis of a kidney can therefore be distinguished from each other, when seen in the field of view of the telescope. Thus, it can be recognized which clamping member corresponds to which finger ring, and the desired clamping member can be moved even if the telescope is twisted and the clamping members look as if they took each other's position.

DESCRIPTION OF THE PREFERRED EMBODIMENTS

Figure 1:
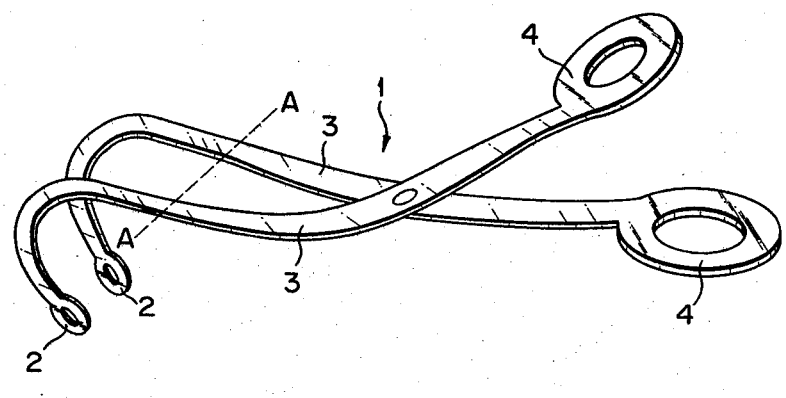
FIGS. 1 and 2 each show a known forceps for extracting stones in the pelvis of a kidney.
Figure 3:
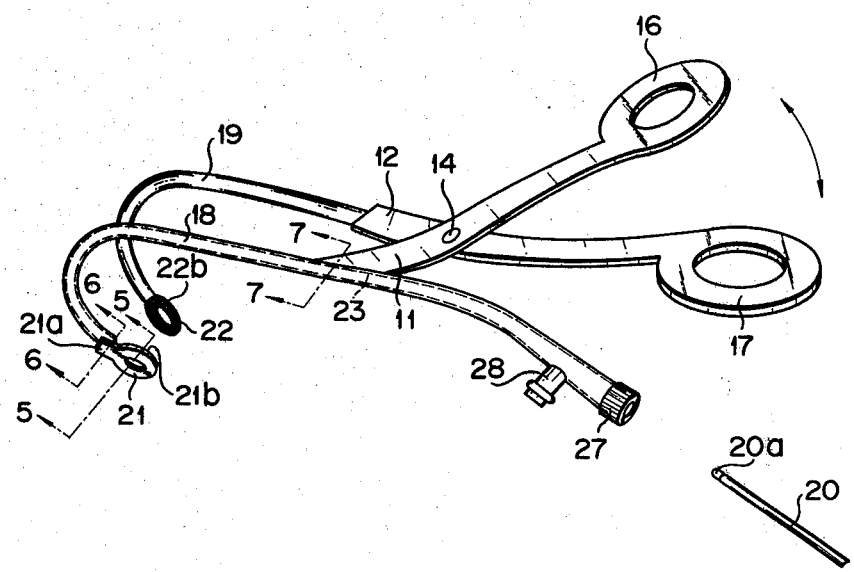
FIG. 3 is a perspective view of a forceps for extracting stones in the pelvis of a kidney, according to one embodiment of this invention.
Figure 2:
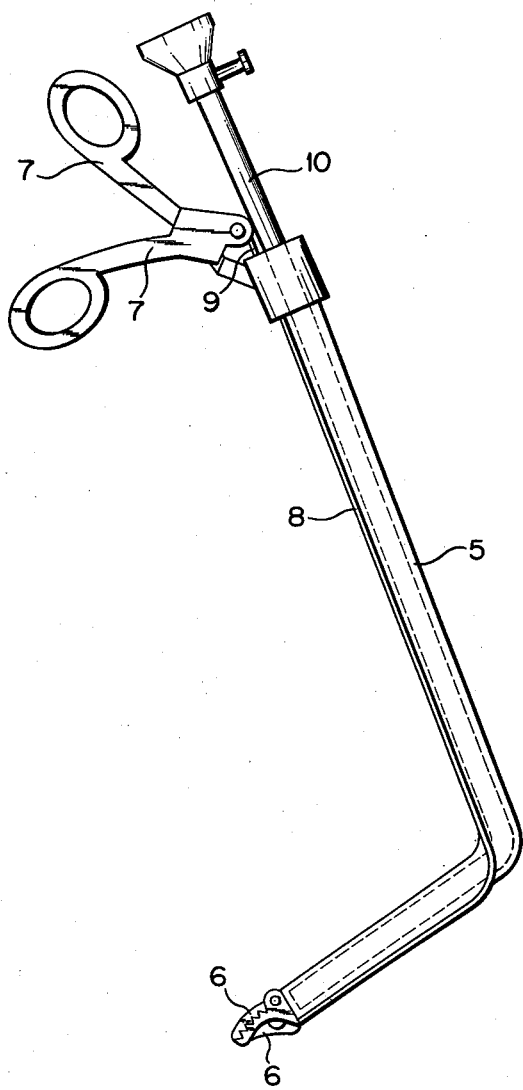

As shown in FIG. 3, the first embodiment of a forceps for extracting stones in the pelvis of a kidney has a pair of shanks 11 and 12 which are pivotally connected to each other by a pin 14 at their intermediate portion. The shank 11 has a finger ring 16 integrally formed with its one end. Likewise, the shank 12 has a finger ring 17 also integrally formed with its one end. To the other end of the shank 11, an arm 18 is secured at its intermediate portion. The arm 18 is a tubular member into which a telescope 20 may be inserted. To the other end of the shank 12 an arm 19 is secured at its proximal end. The arm 19 extends opposite to the finger ring 17. The arms 18 and 19 extend substantially in the same direction, and their distal end portions are curved to deviate in the same direction from the plane in which the finger rings 16 and 17 are moved toward or away from each other.

Figure 4:
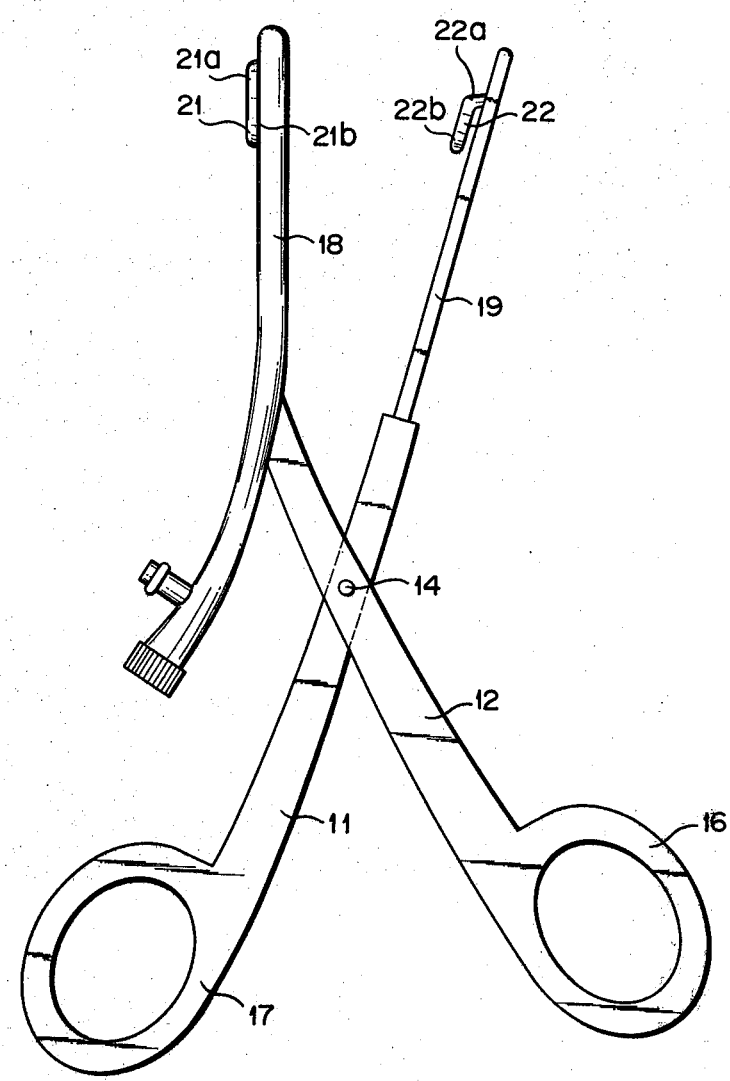
FIG. 4 is a plan view of the forceps shown in FIG. 3.

To the distal end of the arm 18, a stone-clamping member 21 is secured at its protruding portion 21a. Similarly, to the distal end of the arm 19 a stone-clamping member 22 is fixed at its protruding portion 22a. The members 21 and 22 have faces 21b and 22b which face each other. When the members 21 and 22 are ring-shaped, they can clamp a stone easily and firmly. As FIG. 4 illustrates, the stone-clamping member 21 is fixed to the outside periphery of the arm 18 so as not to be disposed right in front of the distal end section 20a of the telescope 20. The stone-clamping member 22 is secured to the distal end of the arm 19 so that it is positioned between the arms 18 and 19 and so that its face 22b is spaced from the inside periphery of the arm 19 for a distance which is substantially equal to the outer diameter of the distal end portion of the arm 19. The faces 21b and 22b of the rings 21 and 22 come into contact when the shanks 11 and 12 are closed.

Figure 5:
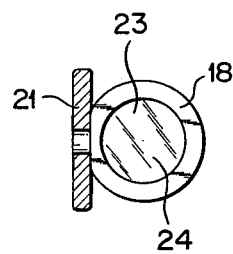
FIG. 5 is a cross sectional view of the forceps of FIG. 3, taken along line 5—5 in FIG. 3.
Figure 6:
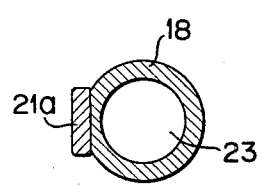
FIG. 6 is a cross-sectional view of the forceps of FIG. 3, taken along line 6—6 in FIG. 3.
Figure 7:
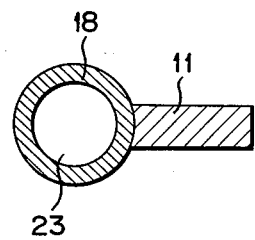
FIG. 7 is a cross sectional view of the forceps of FIG. 3, taken along line 7—7 in FIG. 3.
Figure 8:
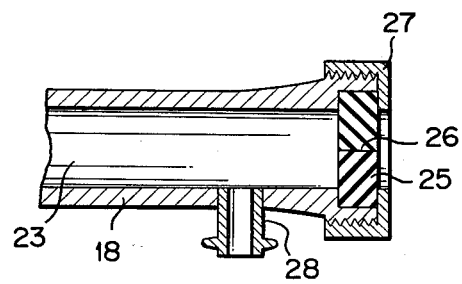
FIG. 8 is a longitudinal cross sectional view of a proximal end portion of a tubular arm into which a telescope of the forceps shown in FIG. 3 is inserted.

A long through hole 23 is provided in the arm 18. In the hole 23, an illumination-observation window 24 made of a transparent material such as glass is provided at the distal end of the arm 18, as illustrated in FIG. 5. As shown in FIG. 8, a disc-shaped sealing member 25 is fitted in the proximal end of the arm 18. The sealing member 25 is made of an elastic material such as rubber and has a cut 26 extending diametrically. A cap 27 having a central hole is screwed onto the proximal end of the arm 18. The cap 27 clamps the proximal end of the arm 18 so that the sealing member 25 is steadily held in the arm 18. A fluid port 28 is provided to communicate with the hole 23 of the arm 18 near the sealing member 25.

The telescope 20 is of a front viewing type which has an observation window and an illumination window in its distal end section 20a. Such telescopes are commonly used in endoscopes and are well known. Thus its structure is not described.

In operation, the telescope 20 is inserted into the arm 18. Then, the finger rings 16 and 17 are moved toward each other to close the arms 18 and 19. Thereafter, the distal end portions of the arms are inserted into the pelvis of a kidney. When the distal ends of the arms 18 and 19 enter the pelvis deep enough, the finger rings 16 and 17 are moved away from each other, thus moving the arms 18 and 19 away from each other so as to bring the stone-clamping member 22 out of the field of view of the telescope 20. Through the telescope 20 and through the window 24 the interior of the pelvis is observed to search for a stone and to know the size and position of a stone, if any. If a stone is found in the pelvis and it is small enough to be clamped between the stone-clamping members 21 and 22, the operator moves the members 21 and 22 toward the stone to allow it to be disposed between the members 21 and 22 while viewing the stone through the telescope 20. The operator then moves the finger rings 16 and 17 toward each other to clamp the stone. Since the members 21, 22 are rings, part of the stone is received by the eye of the member 21, and another part of the stone by the eye of the member 22, whereby the stone is firmly held between the members 21 and 22. Keeping the stone clamped by the members 21 and 22, the operator withdraws the arms 18 and 19 from the pelvis of a kidney, thus extracting the stone out of the pelvis.

It is possible with the forceps of FIG. 3 to clamp a stone in the pelvis of kidney while the operator is observing the stone through the telescope 20 having a wide field of view. Thus, a stone is easily and unfailingly caught and extracted from the pelvis in a very short time, making it unnecessary to keep a patient in pain for a long time or to take a long time for the operator to operate the forceps. The use of the telescope enables the operator to pick up almost every stone in the pelvis, even if the stone cannot be detected by X-rays or if it is small.

Moreover, the movement of the finger rings 16 and 17 is transmitted to the stone-clamping members 21 and 22 not through a flexible member but directly. This ensures a delicate manipulation of the stone-clamping members 21 and 22 and makes it possible to extract from the pelvis without fail a stone which has been once caught between the members 21 and 22.

To supply into the pelvis of a kidney a fluid such as distilled water, liquid medicine, physiological salt water, air or carbon dioxide gas, the telescope 20 is pulled out of the arm 18, and the fluid is introduced through the fluid port 28 and is led to the pelvis through the hole 23 of the arm 18. To remove blood, viscous liquid or the used fluid from the pelvis, the telescope 20 is pulled out of the arm 18, and a suction device (not shown) is connected to the fluid port 28 and operated. Thus, the arm 18 performs two roles, i.e. a channel for the telescope 20 and a fluid passage. When the hole 23 of the arm 18 is used as a fluid passage as well as a channel of the telescope, the window 24 is not provided at the distal end of the arm 18, thereby permitting the hole 23 to communicate with the pelvis.

The sealing member 25 prevents fluid leakage from the hole 23 at the proximal end of the arm 18 when the hole 23 is used as a fluid passage. When the telescope 20 is forcedly inserted into the hole 23 of the arm 18 through the cut 26 of the sealing member 25, the member 25 clamps the telescope 20 resiliently and holds the telescope 20 steadfastly in the hole 23.

In place of the fluid port 28, an inlet aligned with the hole 23 may be provided on the proximal end of the arm 18 so that it functions not only as a fluid port but also as an inlet for inserting the telescope 20 into the hole 23. In this case, a three-way cock may be attached to the proximal end of the arm 18 so that the fluid port 28 is alternatively used as a fluid port and a telescope-guiding inlet.

Figure 9:
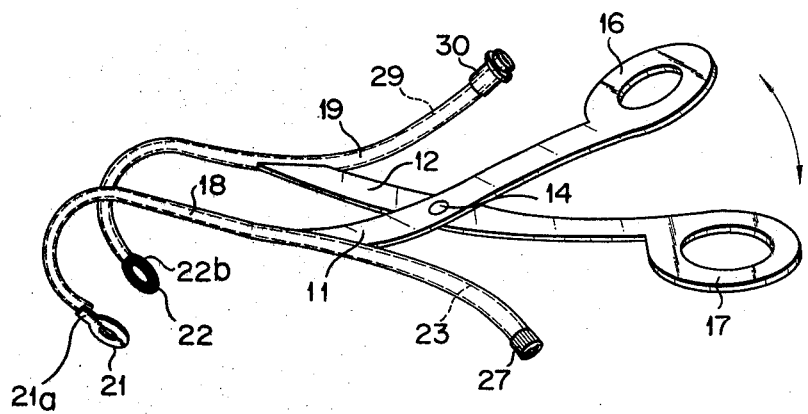
FIG. 9 is a perspective view of another embodiment of this invention.

FIG. 9 shows another embodiment of this invention. This embodiment differs from the forceps of FIGS. 3 to 8 in that one arm 18 is used only for guiding a telescope 20, and the other arm 19 is made of a tubular member and is used only as a fluid passage. The arm 19 has a long through hole 29 and has a fluid port 30 at its proximal end. The hole 29 opens at its distal end. Thus, it is unnecessary with the forceps of FIG. 9 to pull the telescope 20 out of the arm 18 when a fluid is introduced into the pelvis or removed therefrom. Unlike the embodiment of FIGS. 3 to 8, it is unnecessary to clean the hole 23 before using the telescope 20. It therefore requires a shorter time to operate the forceps of FIG. 9 than to use the forceps of FIGS. 3 to 8.

Figure 10:
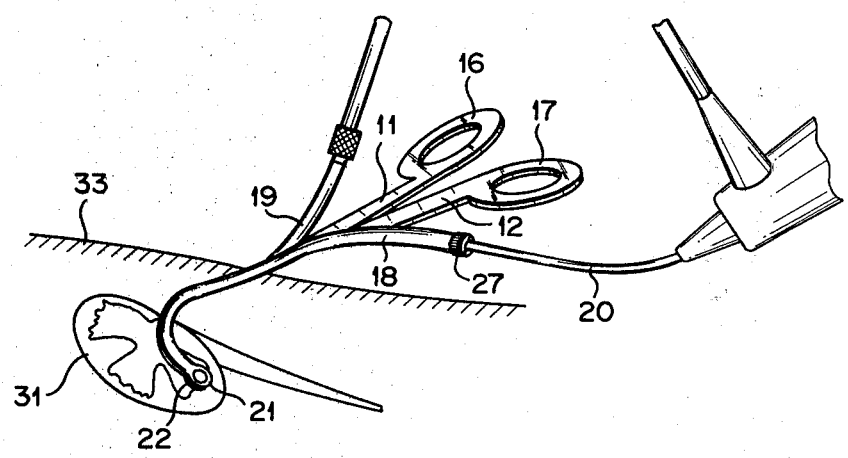
FIGS. 10 and 11 are perspective views of the forceps shown in FIG. 9, illustrating how to use the forceps.
Figure 11:
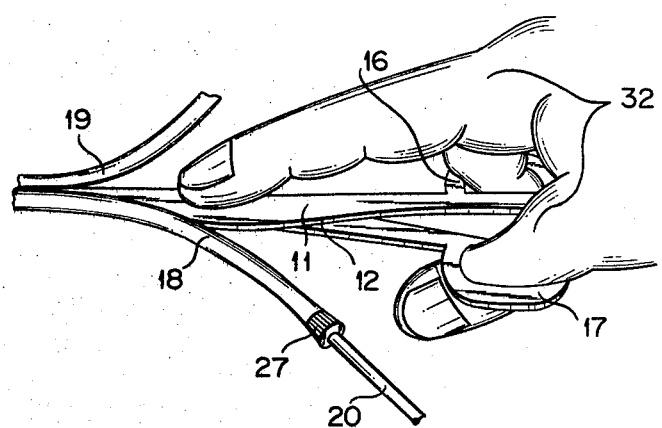
Figure 12:
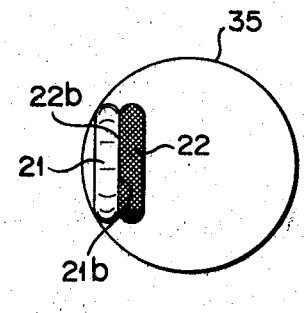
FIGS. 12 and 13 each show the clamping members as seen in the field of view of a telescope.
Figure 13:
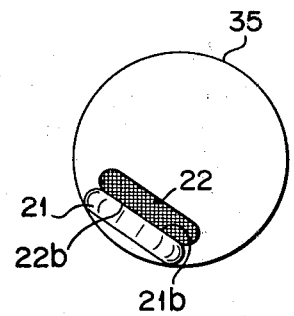

In the forceps of FIG. 9 the proximal end portions of the arms 18 and 19 are positioned substantially in a plane in which shanks 11 and 12 and their finger rings 16 and 17 move, and are curved to be separated from each other and to be disposed out of the operating range of the finger rings 16 and 17. Accordingly, when the forceps is operated in the pelvis of a kidney 31, the proximal end portions of the arms 18, 19 do not contact the operator's fingers 32 or the patient's abdomen 33, whereby the forceps can be operated without being obstructed by the proximal end portions of the arms 18, 19 (FIG. 10 and FIG. 11). Also in the embodiment of FIGS. 3 to 8, the arm 19 is positioned substantially in a plane in which the shanks 11 and 12 and finger rings 16 and 17 move, and is curved so as to be separated from the shanks 11, 12 and finger rings 16, 17 so as not to contact the operator's fingers or the patient's abdomen when the finger rings 16 and 17 are moved.

In both embodiments of FIGS. 3 and 9, the stone-clamping members 21 and 22 may be colored, for example, black and white, respectively, so that the members 21 and 22 in the pelvis of a kidney can be easily distinguished from each other through the telescope 20.

The arms 18 and 19 are extremely thin. For example, their outer diameters are about 2 mm. The telescope 20 is thinner than the arm 18. When the proximal end portion of the telescope 20 which projects out of the arm 18 is rotated, the portion of the endoscope 20 in the arm 18 cannot sufficiently follow the rotation. As a result, the telescope 20 is often twisted in such a way that in the field of view of the telescope 20 the stone-clamping members 21 and 22 look as if they were twisted from the real positions, and that in worst case they look as if their positions were reversed. If the stone-clamping members 21 and 22 are given different colors from each other, they can be distinguished from each other while they are in the pelvis. The operator can therefore easily understand which finger ring he should move. This also helps shorten the time necessary for searching, clamping and extracting a stone in the pelvis of a kidney and avoids an erroneous manipulation of the forceps which would damage the pelvis of a kidney or the wall of the kidney.

What is claimed is:

1. A forceps for extracting stones in the pelvis of a kidney comprising:
   a pair of shanks pivotally connected to each other, each of said shanks having two opposite ends;
   a pair of finger rings, each of said finger rings being coupled to one of said two opposite ends of a respective shank, said finger rings being movable relative to each other in a plane to pivotally move said shanks relative to each other about the pivotal connection of said shanks;
   a pair of elongate arms each secured to the other end of a respective shank, each of said elongate arms having a distal end and a proximal end, the distal end of each elongate arm being more remote from the corresponding finger ring than the proximal end and the distal ends of each elongate arm being curved to deviate from the plane in which said finger rings are movable, at least one of said elongate arms being a tubular member into which a front viewing type telescope is insertable, said at least one tubular elongate arm having an intermediate part connected to said other end of the corresponding shank and having a curved part located between said intermediate part and said proximal end of said at least one elongate arm, said curved part being curved in a direction to extend away from both of said shanks, the direction of curvature of said curved part being that direction in which said curved part is separated in said plane from the finger ring provided on the other shank so that the portion of said tubular elongate arm between said intermediate part and said proximal end is substantially spaced away from said other shank;
   said shank which is connected to said intermediate part of said tubular elongate arm angularly extending away from said tubular elongate arm in a direction opposite to the direction of curvature of said curved part of said tubular elongate arm;
   the pivotal connection of said shanks to each other being spaced a substantial distance from said tubular elongate arm;
   a telescope which is insertable into said at least one tubular elongate arm; and
   a pair of mutually facing stone-clamping members secured to respective distal ends of said elongate arms so as to be in the field of view of a telescope inserted into said tubular elongate arm.

2. The forceps according to claim 1, wherein each of said elongate arms has a portion which is adjacent to said other end of the corresponding shank and lies in said plane in which the finger rings are movable.

3. The forceps according to claim 1 or claim 2, wherein said stone-clamping members have different colors from each other for indicating the corresponding finger rings.

4. The forceps according to claim 1 or claim 2, wherein said distal end of each of said elongate arms extends substantially perpendicularly to said plane in which the finger rings are movable.

5. The forceps according to claim 4, wherein said stone-clamping members have different colors from each other for indicating the corresponding finger rings.

6. The forceps according to claim 1, wherein said tubular elongate arm and said shank which is connected to said intermediate part of said tubular elongate arm form a generally V-shaped configuration relative to each other, the apex of said V-shaped configuration being substantially at said intermediate part of said tubular elongate arm.

* * * * *